(12) United States Patent
Kawano et al.

(10) Patent No.: US 9,545,099 B2
(45) Date of Patent: Jan. 17, 2017

(54) ULTRASONIC ATOMIZING DEVICE AND PEST CONTROL METHOD

(71) Applicant: SUMITOMO CHEMICAL COMPANY, LIMITED, Tokyo (JP)

(72) Inventors: Hiroyuki Kawano, Takarazuka (JP); Tetsuo Harada, Takarazuka (JP); Daisuke Takahata, Ageo (JP); Kazuyuki Ueda, Ageo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 14/366,430

(22) PCT Filed: Dec. 25, 2012

(86) PCT No.: PCT/JP2012/084266
§ 371 (c)(1),
(2) Date: Jun. 18, 2014

(87) PCT Pub. No.: WO2013/100167
PCT Pub. Date: Jul. 4, 2013

(65) Prior Publication Data
US 2015/0122906 A1    May 7, 2015

(30) Foreign Application Priority Data

Dec. 29, 2011   (JP) ................. 2011-290288

(51) Int. Cl.
*B05B 17/04* (2006.01)
*A01N 25/06* (2006.01)
(Continued)

(52) U.S. Cl.
CPC .............. *A01N 25/06* (2013.01); *A01M 1/205* (2013.01); *A01M 29/12* (2013.01); *B05B 17/0646* (2013.01)

(58) Field of Classification Search
CPC ..................................................... A01N 25/06
(Continued)

(56) References Cited

U.S. PATENT DOCUMENTS 6,679,436 B1 *  1/2004  Onishi et al. ................. 239/101
8,296,993 B2 * 10/2012  Modlin et al. ............... 43/132.1
(Continued)

FOREIGN PATENT DOCUMENTS

EP   1 382 399 A1   1/2004
EP   1 773 413 B1   4/2007
(Continued)

OTHER PUBLICATIONS

International Search Report dated Apr. 9, 2013 issued in International Application No. PCT/JP2012/084266.
(Continued)

*Primary Examiner* — Arthur O Hall
*Assistant Examiner* — Adam J Rogers
(74) *Attorney, Agent, or Firm* — Foley & Lardner LLP

(57) ABSTRACT

Micropores penetrating a vibration plate 12 in a thickness direction thereof are formed, in which the vibration plate 12 atomizes a solution by vibration of a piezoelectric vibrator 11 that generates ultrasonic vibration when current is applied thereto. In addition, the spraying time and the spraying interval time are controlled by turning on or off the current applied to the piezoelectric vibrator 11, such that a value of [50% particle diameter of spray particles in cumulative volume distribution]×([spraying time]/[spraying interval time]) becomes 0.2 to 2.5 μm.

10 Claims, 2 Drawing Sheets

(51) Int. Cl.
*B05B 17/00* (2006.01)
*A01M 1/20* (2006.01)
*A01M 29/12* (2011.01)

(58) Field of Classification Search
USPC .................. 239/101.2, 44, 326, 70, 73
See application file for complete search history.

(56) References Cited

U.S. PATENT DOCUMENTS

| | | | |
|---|---|---|---|
| 2007/0237498 A1* | 10/2007 | Helf et al. | 392/386 |
| 2008/0006264 A1 | 1/2008 | Gallem et al. | |
| 2008/0011875 A1* | 1/2008 | Sipinski et al. | 239/102.2 |
| 2008/0073447 A1 | 3/2008 | Wang et al. | |
| 2008/0308096 A1 | 12/2008 | Borgschulte et al. | |
| 2009/0224064 A1* | 9/2009 | Brodbeck et al. | 239/6 |
| 2009/0230208 A1* | 9/2009 | Feriani et al. | 239/4 |
| 2010/0224697 A1* | 9/2010 | Modlin et al. | 239/102.1 |
| 2012/0111970 A1 | 5/2012 | Hogan et al. | |

FOREIGN PATENT DOCUMENTS

| | | | | |
|---|---|---|---|---|
| EP | 2 100 670 A1 | 9/2009 | | |
| JP | 11-056195 A | 3/1999 | | |
| JP | EP 1382399 A1 * | 1/2004 | ......... | A01M 1/2033 |
| JP | 2004-147643 A | 5/2004 | | |
| JP | 2006-121988 A | 5/2006 | | |
| JP | 2009-118792 A | 6/2009 | | |
| JP | 2009-143868 A | 7/2009 | | |
| JP | 2011-75196 A | 4/2011 | | |
| WO | WO-2010/134164 A1 | 11/2010 | | |

OTHER PUBLICATIONS

Office Action issued in U.S. Appl. No. 13/883,840 dated Dec. 19, 2014.
Extended European Search Report issued in co-pending European application No. 13769785 dated Oct. 28, 2015.
Extended European Search Report dated Jul. 10, 2015 issued in Application No. 12862169.5.
Office Action issued in Japanese Patent Application No. 2012-283303 mailed Aug. 30, 2016.

* cited by examiner

ULTRASONIC ATOMIZING DEVICE AND PEST CONTROL METHOD

CROSS REFERENCE TO RELATED APPLICATIONS

This application is the National Phase of PCT/JP2012/084266, filed Dec. 25, 2012, which claims priority to Japanese Application No. 2011-290288, filed Dec. 29, 2011.

TECHNICAL FIELD

The present invention relates to an ultrasonic atomizing device and a pest control method, which are useful for controlling pests.

BACKGROUND ART

As a pest control method, there has been known a pest control method including the step of spraying a solution containing a pest control ingredient into open space. As a method for spraying a solution, there has been known a method using, for instance, an atomizing device that atomizes the solution by simultaneously propelling the solution and a propellant (hereinafter, also referred to as "aerosol type atomization method"). However, since the aerosol type atomization method uses a propellant, it is difficult to reduce the size of the atomizing device.

On the other hand, as a method for spraying a solution without using a propellant, there has been proposed a method using an ultrasonic atomizing device in which a vibration plate having a large number of micropores is placed in contact with a piezoelectric vibrator, and voltage is applied to the piezoelectric vibrator for generating ultrasonic vibration at the piezoelectric vibrator to atomize a solution at the micropores of the vibration plate so as to be sprayed (see, for instance, Patent Literature 1).

CITATION LIST

Patent Literature

PTL 1: Japanese Laid-Open Patent Publication No. 11-56195

SUMMARY OF INVENTION

Technical Problem

However, with the method disclosed in Patent Literature 1, when the particle diameters of the particles of a solution sprayed in open space (particularly in outdoor space) are too small, the solution particles are easily affected by wind and may diffuse too much. As a result, even if a required amount of a pest control ingredient is sprayed, pests within a target area may not be sufficiently controlled.

In addition, if the particle diameters of the solution particles are too large, the sprayed solution particles are not carried by wind and will easily drop to the ground. As a result, the solution may adhere to the vicinity (for instance, approximately a 10 cm range having the atomizing device at the center) of the atomizing device.

The present invention has been made in view of the above described problem, and an object of the present invention is to provide an ultrasonic atomizing device and a pest control method, which are capable of effectively controlling pests in open space (particularly in outdoor space) and reducing adherence of a solution to the vicinity of the atomizing device.

Solution to Problem

The ultrasonic atomizing device of the present invention includes:

a solution reservoir section that stores a solution containing a pest control ingredient, a piezoelectric vibrator that generates ultrasonic vibration when current is applied thereto, a vibration plate that atomizes and sprays the solution with vibration of the piezoelectric vibrator, wherein the vibration plate has micropores penetrating the vibration plate in a thickness direction thereof, and a control section that controls a spraying time and a spraying interval time by turning on or off the current applied to the piezoelectric vibrator, wherein the ultrasonic atomizing device sprays spray-particles of which 50% particle diameter in cumulative volume distribution is 2 to 50 μm, and wherein the control section controls the spraying time and the spraying interval time such that a value of [50% particle diameter of spray particles in cumulative volume distribution]×([spraying time]/[spraying interval time]) (hereinafter, referred to as "formula (I)") becomes 0.2 to 2.5 μm.

According to the ultrasonic atomizing device having such a configuration, spray particles of which 50% particle diameter in cumulative volume distribution is 2 to 50 μm can be generated; and a spraying time and a spraying interval time can be controlled by the control section such that the value of formula (I) becomes 0.2 to 2.5 μm. Therefore, according to the ultrasonic atomizing device, pests can be effectively controlled in open space (particularly in outdoor space) even when particle diameters of spray particles are relatively small (for instance, when 50% particle diameter in cumulative volume distribution is not smaller than 2 μm but smaller than 20 μm). In addition, adherence of the solution to the vicinity of the atomizing device can be reduced even when particle diameters of spray particles are relatively large (for instance, when 50% particle diameter in cumulative volume distribution is 20 to 50 μm).

Thus, as a result of intensive studies in order to solve the above described problem, the present inventors have found that, by setting the spraying interval time and the spraying time in specific ranges, pests can be effectively controlled in open space (particularly in outdoor space) even when particle diameters of spray particles are relatively small, and adherence of the solution to the vicinity of the atomizing device can be reduced even when particle diameters of spray particles are relatively large. Base on these findings, the inventors have arrived at the invention of the present application.

The spraying interval time is preferably 15 to 120 seconds, and more preferably 15 to 60 seconds.

In addition, the spraying time is preferably 0.5 to 5 seconds, and more preferably 0.5 to 3 seconds.

In this case, pests can be effectively controlled in open space (particularly in outdoor space), and adherence of the solution to the vicinity of the atomizing device can be further reduced.

Furthermore, the ultrasonic atomizing device of the present invention preferably further includes a solution supply section that supplies the solution from the solution reservoir section to the vibration plate.

In this case, the solution can be efficiently sprayed upward.

The pest control method of the present invention is a method for controlling pests by using an ultrasonic atomizing device to thereby spray intermittently a solution containing a pest control ingredient, the method including the steps of:

atomizing the solution to generate spray particles of which 50% particle diameter in cumulative volume distribution is 2 to 50 μm, and spraying the spray particles with a spraying time and a spraying interval time that cause the value of formula (I) to be 0.2 to 2.5 μm.

In the pest control method of the present invention, a solution containing a pest control ingredient is atomized by using an ultrasonic atomizing device to generate spray particles of which 50% particle diameter in cumulative volume distribution is 2 to 50 μm, and thereafter the resulting spray particles are sprayed with a spraying time and a spraying interval time that cause the value of formula (I) to be 0.2 to 2.5 μm. Therefore, according to the pest control method of the present invention, a pest can be effectively controlled in open space (particularly in outdoor space) even when particle diameters of spray particles are relatively small, and adherence of the solution to the vicinity of the atomizing device can be reduced even when particle diameters of spray particles are relatively large.

The ultrasonic atomizing device is preferably the previously described ultrasonic atomizing device.

In this case, particle diameters of spray particles can be easily set to desired particle diameters, and the spraying time and the spraying interval time can be easily controlled so as to satisfy a condition of the value of formula (I) being 0.2 to 2.5 μm. Therefore, the pest control method of the present invention can be easily performed.

The pest control ingredient can be at least one ingredient selected from the group consisting of metofluthrin, profluthrin, transfluthrin, meperfluthrin, 2,3,5,6-tetrafluoro-4-(methoxymethyl)benzyl 2,2-dimethyl-3-[(1Z)-3,3,3-trifluoroprop-1-enyl]cyclopropanecarboxylate and dimefluthrin, and preferably metofluthrin.

Advantageous Effects of Invention

According to the ultrasonic atomizing device and the pest control method of the present invention, there is exhibited an excellent effect that pests can be effectively controlled in open space (particularly in outdoor space), and adherence of the solution to the vicinity of the device can be reduced.

DESCRIPTION OF EMBODIMENTS

First, the ultrasonic atomizing device of the present invention will be described with reference to the attached drawings.

Figure 1:
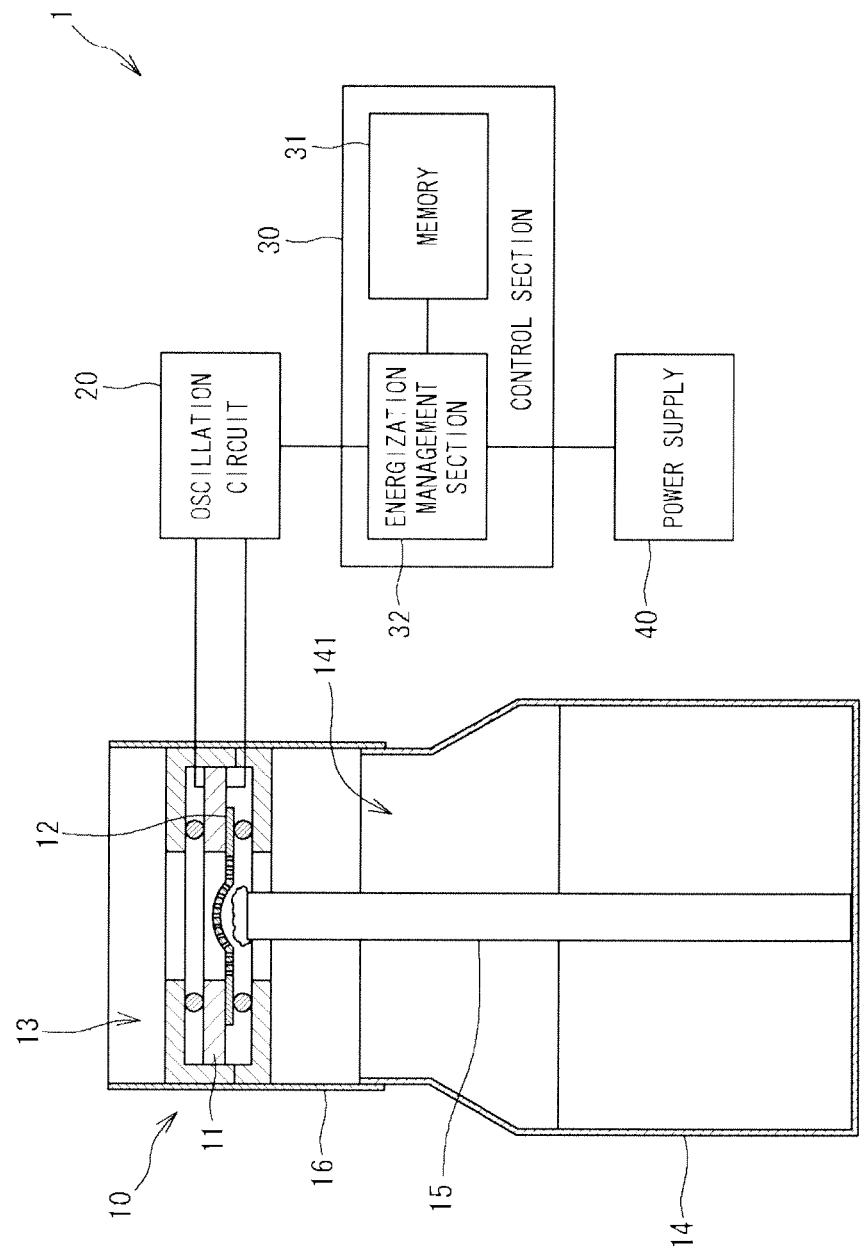
FIG. 1 is a block diagram illustrating a functional configuration of an ultrasonic atomizing device according to one embodiment of the present invention.

FIG. 1 is a block diagram illustrating a functional configuration of an ultrasonic atomizing device according to one embodiment of the present invention. An ultrasonic atomizing device 1 shown in FIG. 1 includes an atomization section 10 for atomizing and spraying a solution containing a pest control ingredient, an oscillation circuit 20 for applying high-frequency voltage to the atomization section 10, a control section 30 for controlling turning on or off the current applied to a piezoelectric vibrator 11 via the oscillation circuit 20, and a power supply 40.

Figure 2:
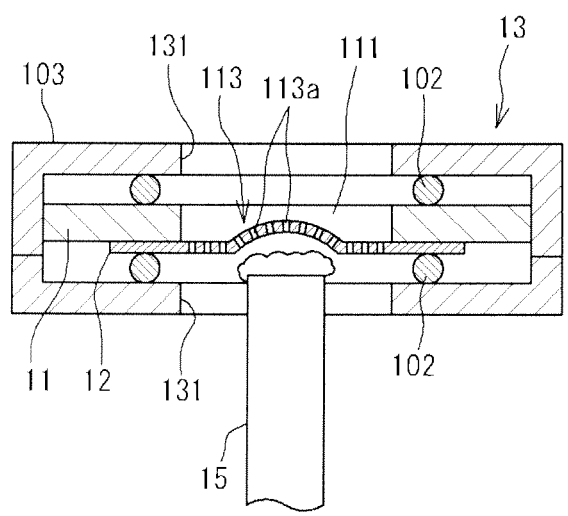
FIG. 2 is an enlarged view of a spraying section of the ultrasonic atomizing device shown in FIG. 1.

As shown in FIG. 2, the atomization section 10 includes: an atomization section main body 13 that atomizes the solution by generating ultrasonic vibration on a vibration plate 12 in association with ultrasonic vibration of the piezoelectric vibrator 11; a solution reservoir section 14 for storing the solution; a solution supply section 15 for supplying the solution from the solution reservoir section 14 to the vibration plate 12 of the atomization section main body 13; and an attachment member 16 for fixing the atomization section main body 13 to the solution reservoir section 14.

The atomization section main body 13 includes: the piezoelectric vibrator 11 for generating ultrasonic vibration when current is applied thereto; the vibration plate 12 for atomizing the solution with vibration from the piezoelectric vibrator 11; and a pair of elastic rings 102 as toric elastic members each which attached to an upper surface of the piezoelectric vibrator 11 and a lower surface of the vibration plate 12; and a casing 103 for elastically sandwiching and holding the piezoelectric vibrator 11 and the vibration plate 12 via the pair of elastic rings 102.

The piezoelectric vibrator 11 is composed of a circular thin-plate shaped piezoelectric ceramic having an opening 111 formed at a central portion thereof. The piezoelectric vibrator 11 is polarized in its thickness direction, and generates ultrasonic vibration in a diameter direction when high-frequency voltage is applied to electrodes (not shown) formed on both surfaces thereof. The piezoelectric vibrator 11 can be, for instance, a piezoelectric vibrator having a thickness of 0.1 to 4.0 mm, an outer diameter of 6 to 60 mm, and an oscillation frequency of 30 to 500 kHz.

The vibration plate 12 includes, for instance, a circular thin board made from nickel. The vibration plate 12 is grafted (adhered) to the lower surface of the piezoelectric vibrator 11 in FIG. 1 in a manner concentric with the piezoelectric vibrator 11 while covering the opening 111 of the piezoelectric vibrator 11. For example, the vibration plate 12 has a thickness of 0.02 to 2.0 mm, and an outer diameter of 6 to 60 mm. The outer diameter of the vibration plate 12 is appropriately selected depending on the size of the piezoelectric vibrator 11 such that the outer diameter is larger than the inner diameter of the opening 111 of the piezoelectric vibrator 11.

Numerous micropores 113a penetrating the vibration plate 12 in the thickness direction thereof are formed at portions of the vibration plate 12 facing the opening 111 of the piezoelectric vibrator 11. From the viewpoint of generating spray particles of which 50% particle diameter in cumulative volume distribution is 2 to 50 μm, the pore diameters of the micropores 113a are preferably 2 to 20 μm, and more preferably 4 to 12 μm.

Provided at the central portion of the vibration plate 12 is a convex part 113 having a curved surface with a top located at said central portion and extending to its hem portions. The convex part 113 has a dome shape swelled in the upward direction (spraying direction of the solution). By having such a shape at the central portion of the vibration plate 12, the solution can be diffused more easily. Associated with expansion and contraction (vibration) of the piezoelectric vibrator 11 in the diameter direction, the convex part 113 generates ultrasonic vibration in the vertical direction.

The vibration plate 12 is placed in contact with or adjacent to the solution supply section 15 for supplying the solution to the vibration plate 12.

Only one pair of the elastic rings 102 are provided. The pair of elastic rings 102 are each placed between the casing 103 and the upper surface of the piezoelectric vibrator 11, and between the casing 103 and the lower surface of the vibration plate 12, in a state of being elastically deformed, respectively being in contact with said upper surface and said lower surface, and respectively being concentric with the piezoelectric vibrator 11 and the vibration plate 12.

As the elastic rings 102, O-rings having a wire diameter of 0.5 to 3 mm, and more preferably a wire diameter of 0.5 to 2.0 mm are suitably used.

Furthermore, the hardness of the elastic rings 102 is 20 to 90 IRHD, and more preferably 30 to 90 IRHD. This allows to hold the piezoelectric vibrator 11 and the vibration plate 12 with a proper elasticity, and effectively suppress excessive vibration of the piezoelectric vibrator 11 and the vibration plate 12. As a result, the solution can be further stably atomized.

The elastic ring 102 placed in contact with the upper surface of the piezoelectric vibrator 11, and the elastic ring 102 placed in contact with the lower surface of the vibration plate 12 preferably have the same mean diameter [(inner diameter+outer diameter)/2]), wire diameter, hardness, and the like; and those having the same mean diameter are particularly desired.

Materials for the elastic rings 102 include, for instance, nitrile rubber, fluororubber, ethylene propylene rubber, silicone rubber, acrylic rubber, hydrogenated nitrile rubber, and the like.

The casing 103 is hollow, toric casing which splits in two so as to be vertically separable; and is formed from a synthetic resin. Inner diameters of openings 131 on the top and bottom surfaces of the casing 103 are configured to be smaller than the inner diameters of the elastic rings 102, such that each of the elastic rings 102 can be each sandwiched and supported between the casing 103 and the piezoelectric vibrator 11 and between the casing 103 and the vibration plate 12. The elastic rings 102 are placed in contact with inner surfaces of the casing 103.

The solution reservoir section 14 includes, for instance, a closed-end cylindrical shaped container having an opening 141 on an upper part thereof. The solution is placed in the solution reservoir section 14. Examples of materials of the solution reservoir section 14 include glass, synthetic resin, and the like.

The solution supply section 15 is made from, for instance, a nonwoven fabric having a cylindrical shape with a diameter of 3 to 4.5 mm, and having its top portion placed adjacent to or in contact with the convex part 113 of the vibration plate 12. A lower-part side of the solution supply section 15 is immersed in the solution in the solution reservoir section 14. The solution supply section 15 can supply the solution to the convex part 113 through capillary action.

The attachment member 16 is cylindrical, and is disposed at an outer circumference of the vicinity of the opening 141 of the solution reservoir section 14 so as to surround the opening 141.

The atomization section main body 13 is fixed to an internal circumference of the attachment member 16.

As shown in FIG. 1, the oscillation circuit 20 is an electric circuit for creating continuous alternating current, and is electrically connected to electrodes (not shown) provided on both surfaces of the piezoelectric vibrator 11. In addition, the oscillation circuit 20 is electrically connected to the control section 30 for controlling turning on or off the current applied to the oscillation circuit 20.

The control section 30 includes: a memory 31 for storing information regarding timing of the current applied to the oscillation circuit 20 based on predetermined spraying time and spraying interval time; and a energization management section 32 for managing turning on or off the current applied to the oscillation circuit 20.

The information stored in the memory 31 is information regarding timing for turning on and off the current applied to the oscillation circuit 20 such that the spraying time becomes 0.5 to 5 seconds, the spraying interval time becomes 15 to 120 seconds, and the value of formula (I) becomes 0.2 to 2.5 µm.

From the viewpoint of suppressing adherence of the solution to the vicinity of the ultrasonic atomizing device, the 50% particle diameter in cumulative volume distribution is 2 to 50 µm, preferably 2 to 30 µm, and more preferably 2.5 to 23 µm.

From the viewpoint of reducing waste of power, the spraying time is 0.5 to 5 seconds, and preferably 0.5 to 3 seconds.

From the viewpoint of obtaining high efficacy and ensuring a fine use feeling, the spraying interval time is 15 to 120 seconds, and preferably 15 to 60 seconds. In the present specification, "spraying interval time" refers to a period of time from a start time of spraying to a start time of the next spraying.

In addition, from the viewpoint of suppressing adherence of the solution to the vicinity of the atomizing device, the value of formula (I) is 0.2 to 2.5 µm, preferably 0.2 to 2.0 µm, and more preferably 0.2 to 1.8 µm.

Here, the 50% particle diameter in cumulative volume distribution in formula (I) can be appropriately set depending on the actual inner diameters of the micropores 113a of the vibration plate 12, the thickness of the vibration plate 12, distances between the micropores 113a adjacent to each other, vibrational amplitude and vibration frequency of the vibration plate 12, viscosity of the solution, and the like. Furthermore, the spraying interval time and the spraying time are configured within the above described ranges such that the value of formula (I) becomes 0.2 to 2.5 µm.

The energization management section 32 receives current from the power supply 40, and turns on or off the current applied to the oscillation circuit 20 based on the information stored in the memory 31.

It should be noted that, instead of the O-rings, the elastic rings 102 used as an elastic member can be rings having a cross-sectional shape of an ellipse, a quadrangle, a triangle, a rhombus, or the like; or can be a ring that is D-shaped, X-shaped, T-shaped, or the like. Furthermore, the elastic rings 102 do not necessary have to be completely continuous in the circumference direction, and can have a single cut in the circumference direction, or can have intermittent cuts at several locations in the circumference direction.

The shape of the convex part 113 of the vibration plate 12 can be any shape. The shape can be not the dome shape of which top portion is formed as a curved surface but also a circular truncated cone shape of which top portion is formed as a flat surface.

Furthermore, in the embodiment described above, although a convex shape vibration plate having the convex part 113 projected in the spraying direction has been illustrated as an example of the vibration plate 12, the vibration plate 12 can be a concave shape vibration plate having the convex part 113 projected opposite of the spraying direction to be a concave part. In addition, the vibration plate 12 can be a flat plate type vibration plate that does not have a convex part and a concave part at the central portion thereof.

In the embodiment described above, although the vibration plate 12 having a circular thin plate shape and completely covering the opening 111 of the piezoelectric vibrator 11 has been illustrated as an example, a rectangular thin-plate shaped vibration plate can be used, and this vibration plate can be extended so as to stretch over the opening 111 of the piezoelectric vibrator 11 to thereby have both ends of the vibration plate fixed on one of the surfaces of the piezoelectric vibrator 11.

In addition, the ultrasonic atomizing device can be one in which the solution is directly supplied to the vibration plate 12 from the solution reservoir section 14 without the solution supply section 15.

The information stored in the memory 31 can be information preset in the memory 31 at the time of manufacturing, or can be information input by a user depending on his/her purpose when the device is used.

Next, the pest control method of the present invention will be described.

One of the significant features of the pest control method of the present invention resides in that a solution containing a pest control ingredient is atomized to generate spray particles of which 50% particle diameter in cumulative volume distribution is 2 to 50 μm, and thereafter the spray particles is sprayed with a spraying time and a spraying interval time that cause the value of formula (I) to be 0.2 to 2.5 μm. Generating the spray particles of which particle diameters are in the above described range, and setting the spraying time and the spraying interval time that cause the value of formula (I) to be 0.2 to 2.5 μm can be easily conducted by using the above described ultrasonic atomizing device. Therefore, in the following, the present invention will be described by using, as an example, a method for controlling pests by using the above described ultrasonic atomizing device, but the present invention is not limited thereto.

Examples of a target pest include an arthropod such as an insect and a tick, and the like. Such arthropod includes, for instance, a pest insect belonging to the order Diptera, a pest insect belonging to the order Lepidoptera, a pest insect belonging to the order Hymenoptera, a pest insect belonging to the order Siphonaptera, a pest insect belonging to the order Isoptera, a pest insect belonging to the order Hemiptera, a pest insect belonging to the order Coleoptera, a pest insect belonging to the order Thysanoptera, a pest insect belonging to the order Orthoptera, a pest insect belonging to the order Acari, and the like, but the present invention is not limited those exemplified ones. Specific examples of the arthropod include those listed in the following (1) to (12), but the present invention is not limited only to those exemplified ones.

(1) Pest Insect Belonging to the Order Diptera

Culex mosquitos such as *Culex pipiens pallens*, *Culex tritaeniorhynchus*, and *Culex quinquefasciatus*; Aedes mosquitoes such as *Aedes aegypti* and *Aedes albopictus*; Anopheles mosquitoes such as *Anopheles sinensis* Wiedemann and *Anopheles gambiae*; Chironomids; Muscids such as *Musca domestica*, *Muscina stabulans*, and *Fannia canicularis*; Calliphorids; Sarcophagids; Anthomyiids such as *Delia platura* and *Delia antiqua*; Tephritids; Drosophilids; Psychodids; Phorids; Tabanids; Simuliids; Stomoxyini flies; Ceratopogonids; and the like.

(2) Pest Insect Belonging to the Order Lepidoptera

Pyralids such as *Chilo suppressalis*, *Cnaphalocrocis medinalis* Guenee, and *Plodia interpunctella*; Noctuids such as *Spodoptera litura*, *Mythimna separata*, and *Mamestra brassicae*; Pierids such as *Pieris rapae*; Tortricids such as *Adoxophyes orana*; Carposinids; Lyonetiids; Lymantriids; Autographa moths; a pest insect belonging to the genus *Agrotis* (*Agrotis* sp.) such as *Agrotis segetum* and *Agrotis ipsilon*; a pest insect belonging to the genus *Helicoverpa* (*Helicoverpa* sp.); a pest insect belonging to the genus *Heliothis* (*Heliothis* sp.); *Plutella xylostella*, *Parnara guttata*, *Tinea translucens* Meyrick, *Tineola bisselliella*, and the like.

(3) Pest Insect Belonging to the Order Dictyoptera

*Blattella germanica*, *Periplaneta fuliginosa*, *Periplaneta americana*, *Periplaneta australasiae*, *Periplaneta brunnea* Burmeister, *Blatta orientalis*, and the like.

(4) Pest Insect Belonging to the Order Hymenoptera

Formicids, and bees and wasps (Polistinae wasps such as *Polistes chinensis*, *Polistes riparius*, *Polistes jadwigae*, *Polistes rothneyi*, *Polistes mandarinus*, *Polistes snelleni*, and *Polistes japonicus*; Vespinae wasps such as *Vespa mandarinia*, *Vespa simillima*, *Vespa analis* Fabriciusi, *Vespa crabro*, *Vespa ducalis*, *Vespula flaviceps*, *Vespula shidai*, and *Dolichovespula media*; Bethylids; carpenter bees; Pompilids; Sphecids; potter wasps; and the like), and the like.

(5) Pest Insect Belonging to the Order Siphonaptera

*Ctenocephalides canis*, *Ctenocephalides felis*, *Pulex irritans*, and the like.

(6) Pest Insect Belonging to the Order Anoplura

*Pediculus humanus*, *Phthirus pubis*, *Pediculus humanus capitis*, *Pediculus humanus corporis*, and the like.

(7) Pest Insect Belonging to the Order Isoptera

*Reticuliteunes speratus*, *Coptotermes formosanus*, and the like.

(8) Pest Insect Belonging to the Order Hemiptera

Delphacids such as *Laodelphax striatellus*, *Nilaparvata lugens*, and *Sogatella furcifera* Horvath; Cicadellids such as *Nephotettix cincticeps* and *Nephotettix virescens*; Aphids; Pentatomids; Aleyrodids; Coccoideas; Tingids; Psyllids; Cimicids; and the like.

(9) Pest Insect Belonging to the Order Coleoptera

*Attagenus japonicus*, *Anthrenus verbasci*; Diabrotica beetles such as *Diabrotica virgifera virgifera*, and *Diabrotica undecimpunctata howardi*; Scarabaeids such as *Anomala cuprea*, and *Anomala rufocuprea*; Curculionoids such as *Sitophilus zeamais*, *Lissorhoptrus oryzophilus*, *Anthonomus grandis*, and *Callosobruchus chinensis*; Tenebrionids such as *Tenebrio molitor*, and *Tribolium castaneum*; Chrysomelids such as *Oulema oryzae*, *Phyllotreta striolata*, and *Aulacophora femoralis*; Anobiids; an insect belonging to the genus *Epilachna* (*Epilachna* sp.) such as *Epilachna vigintioctopunctata*; Lyctids; Bostrichids; Cerambycids; *Paederus fuscipes* Curtis; and the like.

(10) Pest Insect Belonging to the Order Thysanoptera

*Thrips palmi*; *Frankliniella occidentalis* (PERGANDE); *Thrips hawaiiensis*; and the like.

(11) Pest Insect Belonging to the Order Orthoptera

Mole crickets, grasshoppers, and the like.

(12) Pest Insect Belonging to the Order Acari

Pyroglyphids such as *Dermatophagoides farinae* and *Dermatophagoides pteronyssinus*; Acarids such as *Tyrophagus putrescentiae* and *Aleuroglyphus ovatus*; Glycyphagids such as *Glycyphagus privatus, Glycyphagus domesticus,* and *Glycyphagus destructor*; Cheyletids such as *Cheyletus malaccensis* and *Cheyletus malaccesis*; Tarsonemids; Chortoglyphids; Haplochthoniids; Tetranychids such as *Tetranychus urticae, Tetranychus kanzawai, Panonychus citri* (McGregor), and *Panonychus ulmi*; Ixodids such as *Haemaphysalis longicornis*; and the like.

The solution contains a pest control ingredient. Examples of the pest control ingredient include synthetic pyrethroid compounds, organophosphorus compounds, carbamate compounds, nereistoxin compounds, neonicotinoid compounds, benzoyl urea compounds, phenylpyrazole compounds, Bt toxin insecticides, hydrazine compounds, chlorinated organic compounds, natural insecticides, other insecticides, other repellents and the like, but the present invention is not limited only to those exemplified ones. In the present invention, the pest control ingredient and a synergist can be used in combination. Specific examples of the pest control ingredient and the synergist include those listed in the following (1) to (14), but the present invention is not limited only to those exemplified ones.

(1) Synthetic Pyrethroid Compounds

Acrinathrin, allethrin, beta-cyfluthrin, bifenthrin, cycloprothrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, meperfluthrin, 2,3,5,6-tetrafluoro-4-(methoxymethyl)benzyl 2,2-dimethyl-3-[(1Z)-3,3,3-trifluoroprop-1-enyl]cyclopropanecarboxylate, dimefluthrin, 2,3,5,6-tetrafluoro-4-methylbenzyl=2,2-dimethyl-3-(1-propenyl)cyclopropanecarboxylate, 2,3,5,6-tetrafluoro-4-(methoxymethyl)benzyl=2,2-dimethyl-3-(2-methyl-1-propenyl)cyclopropanecarboxylate, 2,3,5,6-tetrafluoro-4-(methoxymethyl)benzyl=2,2,3,3-tetramethylcyclopropanecarboxylate, 2,3,5,6-tetrafluoro-4-(methoxymethyl)benzyl 2,2-dimethyl-3-(3,3,3-trifluoroprop-1-enyl)cyclopropanecarboxylate and the like.

(2) Organophosphorus Compounds

Acephate, Aluminium phosphide, butathiofos, cadusafos, chlorethoxyfos, chlorfenvinphos, chlorpyrifos, chlorpyrifos-methyl, cyanophos (CYAP), diazinon, dichlorodiisopropyl ether (DCIP), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, Hydrogen phosphide, isofenphos, isoxathion, malathion), mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos, and the like.

(3) Carbamate Compounds

Alanycarb, bendiocarb, benfuracarb, fenobcarb [Methylcarbamic acid o-(sec-butyl)phenyl (BPMC)], carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, 1-naphthyl-N-methyl carbamate (NAC), oxamyl, pirimicarb, propoxur (PHC), 3,5-xylylmethylcarbamate (XMC), thiodicarb, xylylcarb, aldicarb, and the like.

(4) Nereistoxin Compounds

Cartap, bensultap, thiocyclam, monosultap, bisultap, and the like.

(5) Neonicotinoid Compounds

Imidacloprid, nitenpyram, acetamiprid, thiamethoxam, thiacloprid, dinotefuran, clothianidin, and the like.

(6) Benzoylurea Compounds

Chlorfluazuron, bistrifluron, diafenthiuron, diflubenzuron, fluazuron, flucycloxuron, flufenoxuron, hexaflumuron, lufenuron, novaluron, noviflumuron, teflubenzuron, triflumuron, triazuron, and the like.

(7) Phenylpyrazole Compounds

Aacetoprole, ethiprole, fipronil, vaniliprole, pyriprole, pyrafluprole, and the like.

(8) Bt Toxin Insecticides

Living spores of *Bacillus thuringiensis* and crystal toxin produced by *Bacillus thuringiensis*, and mixture thereof.

(9) Hydrazine Compounds

Chromafenozide, halofenozide, methoxyfenozide, tebufenozide, and the like.

(10) Chlorinated Organic Compounds

Aldrin, dieldrin, dienochlor, endosulfan, methoxychlor, and the like.

(11) Natural Insecticides

Machine oil, nicotine-sulfate, and the like.

(12) Other Insecticides

Avermectin-B, bromopropylate, buprofezin, chlorphenapyr, cyromazine, D-D(1,3-Dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, Arsenic acid, benclothiaz, Calcium cyanamide, Calcium polysulfide, chlordane, Dichlorodiphenyltrichlorethane (DDT), 3,3'-Dithiobis (propanoic acid succinimidyl (DSP), flufenerim, flonicamid, flurimfen, formetanate, metam-ammonium, metam-sodium, Methyl bromide, Potassium oleate, protrifenbute, spiromesifen, Sulfur, metaflumizone, spirotetramat, pyrifluquinazone, spinetoram, chlorantraniliprole, tralopyril, and the like.

(13) Other Repellent

N,N-Diethyl-m-toluamide, limonene, linalool, citronellal, menthol, menthone, Hinokitiol, geraniol, eucalyptol, indoxacarb, carane-3,4-diol, 2,5-pyridinedicarboxylic acid dipropyl (MGK-R-326), 2-(octylthio)ethanol (MGK-R-874), BAY-KBR-3023, and the like.

(14) Synergist

5-[[2-(2-Butoxyethoxy)ethoxy]methyl]-6-propyl-1,3-benzodioxole, N-(2-ethylhexyl)bicyclo[2.2.1]hept-5-ene-2,3-dicarboximide, octachlorodipropylether, isobornyl thiocyanoacetate, N-(2-ethylhexyl)-1-isopropyl-4-methylbicyclo[2.2.2]oct-5-ene-2,3-dicarboximide, and the like.

Among the pest control ingredients, from the viewpoint of being easily volatilized and being able to effectively control pests, metofluthrin, profluthrin, transfluthrin, meperfluthrin, 2,3,5,6-tetrafluoro-4-(methoxymethyl)benzyl 2,2-dimethyl-3-[(1Z)-3,3,3-trifluoroprop-1-enyl]cyclopropanecarboxylate, and dimefluthrin are preferable, and metofluthrin is more preferable. In addition, those described above can be used alone or in admixture of two or more kinds.

When the pest control ingredient is a liquid, the pest control ingredient can be sprayed as is, or can be diluted in a solvent to be sprayed. In addition, when the pest control ingredient is a solid, it can be dissolved in a solvent to be sprayed.

Examples of the solvent used for diluting or dissolving the pest control ingredient include aromatic or aliphatic hydrocarbons, halogenated hydrocarbons, alcohols, ethers, esters, ketones, nitriles, sulfoxides, acid amides, alkylidene carbonates, plant oil, plant essential oil, and water; however, the present invention is not limited only to those illustrative examples. Specific examples of the solvent include those listed in the following (1) to (13), but the present invention is not limited only to those exemplified ones.

(1) Aromatic or Aliphatic Hydrocarbons

Xylene, toluene, alkyl naphthalene, phenylxylyl ethane, kerosene, light gas oil, hexane, cyclohexane, and the like;

(2) Halogenated Hydrocarbons

Chlorobenzene, dichloromethane, dichloroethane, trichloroethane, and the like;

(3) Alcohols

Methanol, ethanol, isopropyl alcohol, butanol, hexanol, benzyl alcohol, ethylene glycol, and the like;

(4) Ethers

Diethyl ether, Ethylene glycol dimethyl ether, diethylene glycol monomethyl ether, diethylene glycol monoethyl ether, propylene glycol monomethyl ether, tetrahydrofuran, dioxane, and the like;

(5) Esters

Ethyl acetate, butyl acetate, and the like;

(6) Ketones

Acetone, methyl ethyl ketone, methyl isobutyl ketone, cyclohexanone, and the like;

(7) Nitriles

Acetonitrile, isobutyronitrile, and the like;

(8) Sulfoxides dimethyl sulfoxide, and the like;

(9) Acid Amides

N,N-Dimethyl formamide, N,N-dimethylacetamide, N-methyl-pyrrolidone, and the like;

(10) Alkylidene Carbonates

Propylene carbonate, and the like;

(11) Plant Oil

Soy oil, cotton seed oil, and the like;

(12) Plant Essential Oil

Orange oil, hyssop oil, lemon oil, and the like.

The content of the pest control ingredient in the solution can be any amount as long as it is sufficient for controlling pests when the solution is sprayed. Specifically, from the viewpoint of ensuring sufficient efficacy and reducing product cost, the amount of the pest control ingredient in the solution is preferably 0.01 to 10% by mass, and more preferably 0.1 to 5% by mass.

The respective ranges for the 50% particle diameter in cumulative volume distribution, the spraying time, and the spraying interval time are the same as the respective ranges for the 50% particle diameter in cumulative volume distribution, the spraying time, and the spraying interval time for the above described ultrasonic atomizing device. The 50% particle diameter in cumulative volume distribution is determined depending on the 50% particle diameter in cumulative volume distribution of spray particles sprayed by the used ultrasonic atomizing device.

When the above described ultrasonic atomizing device is set in a certain space in which target pests are existed, and thereafter its power is turned on, the current applied to the piezoelectric vibrator 11 is turned on or off by the control section 30 to set the spraying time and the spraying interval time such that the value of formula (I) becomes 0.2 to 2.5 µm. When the current applied to the piezoelectric vibrator 11 is turned on and high-frequency voltage is applied to the piezoelectric vibrator 11, ultrasonic vibration is generated on the piezoelectric vibrator 11 to further vibrate the convex part 113 of the vibration plate 12. At this time, the solution supplied to the convex part 113 via the solution supply section 15 is introduced to the micropores 113a of the convex part 113 through capillary action, atomized to become spray particles of which 50% particle diameter in cumulative volume distribution is 2 to 50 µm, and sprayed upward for a predetermined spraying time. On the other hand, when the current applied to the piezoelectric vibrator 11 is turned off, spraying of the solution stops. With this, the solution can be sprayed as spray particles of which 50% particle diameter in cumulative volume distribution is 2 to 50 µm with the spraying time and the spraying interval time that cause the value of formula (I) to be 0.2 to 2.5 µm.

Therefore, according to the pest control method, pests can be effectively controlled in open space (particularly in outdoor space), and adherence of the solution to the vicinity of the ultrasonic atomizing device can be reduced.

In the present invention, a general ultrasonic atomizing device can be used instead of the ultrasonic atomizing device of the present invention. Also in this case, a solution containing a pest control ingredient can be atomized to generate spray particles of which 50% particle diameter in cumulative volume distribution is 2 to 50 μm, and sprayed with a spraying time and a spraying interval time that cause the value of formula (I) to be 0.2 to 2.5 μm.

EXAMPLE

In the following, the present invention will be more specifically described on the basis of Examples, but the present invention is not limited thereto.

Production Example 1

Preparation of Solution

A solution was prepared by dissolving metofluthrin (commercial name: Eminence, manufactured by Sumitomo Chemical Co., Ltd.) as a pest control ingredient in a solvent (commercial name: EXXSOL D110, manufactured by Exxon Mobil Corp.). A solution spray volume per 20 minutes was calculated by using a solution spray volume per spray, and thereafter the content of metofluthrin in the solution was set such that the same amount of metofluthrin will be sprayed under all test conditions.

Production Example 2

Preparation of Ultrasonic Atomizing Device

An ultrasonic type atomizing device having the following specification was prepared. The ultrasonic type atomizing device of the present Example is a device having the same structure as the ultrasonic type atomizing device shown in FIG. 1 except for the configuration of the following (5).
(1) Piezoelectric vibrator 11: A piezoelectric ceramic having an outer diameter of 15 mm, an inner diameter of 5 mm, and a thickness of 0.4 mm.
(2) Vibration plate: Convex shape vibration plate
  Thickness: 0.04 mm (made from nickel)
  Diameter of base end of convex part: 3 mm
  Internal diameters of micropores at convex part: Set as shown in Tables 1 to 6.
(3) Applied voltage: 40 Vp-p
(4) Frequency of piezoelectric vibrator 11 (ultrasonic excitation machine): 110 kHz
(5) Setting of current applied to piezoelectric vibrator 11 (ultrasonic excitation machine): Freely configurable by selecting from intermittent-driving at an interval of 5 to 180 seconds and continuous-driving at a per-spray driving time of 0.1 to 10 seconds.
(6) 50% particle diameter of spray particles in cumulative volume distribution: "Spray particle diameter" in Tables 1 to 6 should be referred to.

Particle diameters of spray particles were measured by using a particle size analyzer (commercial name: AEROTRAC SPR, manufactured by Nikkiso Co., Ltd.).

Test Example 1

(1) Evaluation of Repellence Rate

The solution obtained in Production Example 1 was placed in the solution reservoir section 14 of the ultrasonic atomizing device obtained in Production Example 2, and the ultrasonic atomizing device was installed in open space. Turning on and off the current applied to the oscillation circuit 20 by the control section 30 was set to obtain the spraying time and the spraying interval (spraying interval time) as shown in Tables 1 to 6. After 20 minutes from the start of the first spraying of the solution, reduction in pest density (hereinafter, repellence rate) was obtained at a location 3.6 m away from the installation location of the ultrasonic atomizing device. The repellence rate was calculated in accordance with the following formula (II):

$$(([\text{Density of pests before spraying the solution}] - [\text{Density of pests after 20 minutes from the start of the first spraying of the solution}])/[\text{Density of pests before spraying the solution}]) \times 100 \qquad \text{(II)}$$

The results are shown in Tables 1 to 6.
(2) Evaluation of Adherence Level of Solution The solution obtained in Production Example 1 was placed in the solution reservoir section 14 of the ultrasonic atomizing device obtained in Production Example 2, and the ultrasonic atomizing device was installed in open space. Turning on and off the current applied to the oscillation circuit 20 by the control section 30 was set to obtain the spraying time and the spraying interval (spraying interval time) as shown in Tables 1 to 6. After 20 minutes from the start of the first spraying of the solution, the area of the part (solution adherence part) where the solution has adhered was measured in a 6 cm radius range (range A) having the spray openings (the openings 131 in FIG. 2) of the ultrasonic atomizing device as a center thereof.

The following evaluation criteria were used.
<Evaluation Criteria>
"S" (Very Good): Proportion of the area of the solution adherence part with respect to range A is less than 10%.
"A" (Good): Proportion of the area of the solution adherence part with respect to range A is not less than 10% but less than 30%.
"B" (Average): Proportion of the area of the solution adherence part with respect to range A is not less than 30% but less than 50%.
"C" (bad): Proportion of the area of the solution adherence part with respect to range A is not less than 50%.

TABLE 1

| | Inner Diameter of Microscope (μm) | Spray Particle Diameter $D_{50}$ (μm) | Spraying Time (second/spray) | Interval Time (second) | Spraying Time/ Interval Time A | Spray Particle Diameter × A | Repellence Rate (%) (3.6 m) | Solution Adherence |
|---|---|---|---|---|---|---|---|---|
| Example 1 | 4 | 2.5 | 3.4 | 30 | 0.11 | 0.28 | 95 | S |
| Example 2 | 4 | 2.5 | 5.0 | 30 | 0.17 | 0.42 | 100 | S |
| Example 3 | 4 | 2.5 | 5.0 | 15 | 0.33 | 0.83 | 100 | A |
| Example 4 | 4 | 2.5 | 5.0 | 60 | 0.08 | 0.21 | 94 | S |

TABLE 1-continued

|  | Inner Diameter of Microscope (μm) | Spray Particle Diameter $D_{50}$ (μm) | Spraying Time (second/spray) | Interval Time (second) | Spraying Time/ Interval Time A | Spray Particle Diameter × A | Repellence Rate (%) (3.6 m) | Solution Adherence |
|---|---|---|---|---|---|---|---|---|
| Comparative Example 1 | 4 | 2.5 | 1.0 | 15 | 0.07 | 0.17 | 60 | S |
| Comparative Example 2 | 4 | 2.5 | 4.0 | 60 | 0.07 | 0.17 | 73 | S |

TABLE 2

|  | Inner Diameter of Microscope (μm) | Spray Particle Diameter $D_{50}$ (μm) | Spraying Time (second/spray) | Interval Time (second) | Spraying Time/ Interval Time A | Spray Particle Diameter × A | Repellence Rate (%) (3.6 m) | Solution Adherence |
|---|---|---|---|---|---|---|---|---|
| Example 5 | 7 | 11 | 0.5 | 15 | 0.03 | 0.37 | 95 | S |
| Example 6 | 7 | 11 | 2.8 | 30 | 0.09 | 1.03 | 100 | A |
| Example 7 | 7 | 11 | 5.0 | 30 | 0.17 | 1.83 | 100 | B |
| Comparative Example 3 | 7 | 11 | 5.0 | 15 | 0.33 | 3.67 | 100 | C |

TABLE 3

|  | Inner Diameter of Microscope (μm) | Spray Particle Diameter $D_{50}$ (μm) | Spraying Time (second/spray) | Interval Time (second) | Spraying Time/ Interval Time A | Spray Particle Diameter × A | Repellence Rate (%) (3.6 m) | Solution Adherence |
|---|---|---|---|---|---|---|---|---|
| Example 8 | 8 | 16 | 0.5 | 30 | 0.02 | 0.27 | 98 | S |
| Example 9 | 8 | 16 | 5.0 | 60 | 0.08 | 1.33 | 100 | A |
| Comparative Example 4 | 8 | 16 | 5.0 | 30 | 0.16 | 2.56 | 100 | C |

TABLE 4

|  | Inner Diameter of Microscope (μm) | Spray Particle Diameter $D_{50}$ (μm) | Spraying Time (second/spray) | Interval Time (second) | Spraying Time/ Interval Time A | Spray Particle Diameter × A | Repellence Rate (%) (3.6 m) | Solution Adherence |
|---|---|---|---|---|---|---|---|---|
| Example 10 | 10 | 23 | 0.5 | 30 | 0.02 | 0.38 | 92 | S |
| Example 11 | 10 | 23 | 1.0 | 60 | 0.02 | 0.38 | 92 | S |
| Example 12 | 10 | 23 | 1.5 | 30 | 0.05 | 1.15 | 100 | A |
| Comparative Example 5 | 10 | 23 | 0.5 | 60 | 0.01 | 0.19 | 53 | S |
| Comparative Example 6 | 10 | 23 | 3.0 | 30 | 0.10 | 2.30 | 100 | C |

TABLE 5

|  | Inner Diameter of Microscope (μm) | Spray Particle Diameter $D_{50}$ (μm) | Spraying Time (second/spray) | Interval Time (second) | Spraying Time/ Interval Time A | Spray Particle Diameter × A | Repellence Rate (%) (3.6 m) | Solution Adherence |
|---|---|---|---|---|---|---|---|---|
| Example 13 | 12 | 30 | 0.5 | 60 | 0.01 | 0.25 | 94 | S |
| Example 14 | 12 | 30 | 3.5 | 60 | 0.06 | 1.75 | 100 | B |
| Comparative Example 7 | 12 | 30 | 3.0 | 30 | 0.10 | 3.00 | 100 | C |

TABLE 6

|  | Inner Diameter of Microscope (μm) | Spray Particle Diameter $D_{50}$ (μm) | Spraying Time (second/spray) | Interval Time (second) | Spraying Time/ Interval Time A | Spray Particle Diameter × A | Repellence Rate (%) (3.6 m) | Solution Adherence |
|---|---|---|---|---|---|---|---|---|
| Example 15 | 15 | 50 | 0.5 | 60 | 0.01 | 0.42 | 96 | S |
| Example 16 | 15 | 50 | 0.5 | 15 | 0.03 | 1.67 | 100 | B |
| Example 17 | 15 | 50 | 2.0 | 60 | 0.03 | 1.67 | 100 | B |
| Comparative Example 8 | 15 | 50 | 1.0 | 15 | 0.07 | 3.33 | 100 | C |

It can be understood from the results shown in Tables 1 to 6 that high repellence rates can be ensured and adherence of the solution to the vicinity of the ultrasonic atomizing device is small, when the value of the formula (I) ("Spray Particle Diameter×A" in the Tables) is within a range of 0.2 to 2.5 μm.

It can be understood from the results described above that a pest can be effectively controlled in open space (particularly in outdoor space) and adherence of the solution to the vicinity of the ultrasonic atomizing device can be reduced, by atomizing the solution containing the pest control ingredient to generate spray particles of which 50% particle diameter in cumulative volume distribution is 2 to 50 μm, and by setting the spraying time to be 0.5 to 5 seconds and the spraying interval time to be 15 to 60 seconds and setting the spraying time and the spraying interval time such that the value of formula (I) becomes 0.2 to 2.5 μm.

REFERENCE SIGNS LIST 1 ultrasonic atomizing device
11 piezoelectric vibrator
12 vibration plate
14 solution reservoir section
15 solution supply section
30 control section
113a micropores

The invention claimed is:

1. A method for controlling pests in open space by using an ultrasonic atomizing device to thereby spray intermittently a solution containing a pest control ingredient, the method comprising the steps of:
atomizing the solution to generate spray particles of which 50% particle diameter in cumulative volume distribution is 2 to 50 μm; and
spraying the spray particles in open space with a spraying time and a spraying interval time that cause a value of [50% particle diameter of spray particles in cumulative volume distribution]×([spraying time]/[spraying interval time]) to be 0.2 to 2.0 μm.

2. The method according to claim 1, wherein the ultrasonic atomizing device is an ultrasonic atomizing device comprising:
a solution reservoir section that stores a solution containing a pest control ingredient,
a piezoelectric vibrator that generates ultrasonic vibration when current is applied thereto,
a vibration plate that atomizes and sprays the solution with vibration of the piezoelectric vibrator, wherein the vibration plate has micropores penetrating the vibration plate in a thickness direction thereof, and
a control section that controls a spraying time and a spraying interval time by turning on or off the current applied to the piezoelectric vibrator,
wherein the ultrasonic atomizing device sprays spray-particles of which 50% particle diameter in cumulative volume distribution is 2 to 50 μm, and
wherein the control section controls the spraying time and the spraying interval time such that a value of [50% particle diameter of spray particles in cumulative volume distribution]×([spraying time]/[spraying interval time]) becomes 0.2 to 2.0 μm.

3. The method according to claim 1, wherein the pest control ingredient is at least one ingredient selected from the group consisting of metofluthrin, profluthrin, transfluthrin, meperfluthrin, 2,3,5,6-tetrafluoro-4-(methoxymethyl)benzyl 2,2-dimethyl-3-[(1Z)-3,3,3-trifluoroprop-1-enyl]cyclopropanecarboxylate and dimefluthrin.

4. The method according to claim 1, wherein the pest control ingredient is metofluthrin.

5. The method according to claim 1, wherein the ultrasonic atomizing device is an ultrasonic atomizing device comprising:
a solution reservoir section that stores a solution containing a pest control ingredient,
a piezoelectric vibrator that generates ultrasonic vibration when current is applied thereto,
a vibration plate that atomizes and sprays the solution with vibration of the piezoelectric vibrator, wherein the vibration plate has micropores penetrating the vibration plate in a thickness direction thereof, and
a control section that controls a spraying time and a spraying interval time by turning on or off the current applied to the piezoelectric vibrator,
wherein the ultrasonic atomizing device sprays spray-particles of which 50% particle diameter in cumulative volume distribution is 2 to 50 μm, and
wherein the control section controls the spraying time and the spraying interval time such that a value of [50% particle diameter of spray particles in cumulative volume distribution]×([spraying time]/[spraying interval time]) becomes 0.2 to 2.0 μm and
further comprising a solution supply section that supplies the solution from the solution reservoir section to the vibration plate.

6. The method according to claim 1, further comprising a solution supply section that supplies the solution from the solution reservoir section to the vibration plate.

7. The method according to claim 1, wherein the spraying interval time is 15 to 120 seconds.

8. The method according to claim 1, wherein the spraying interval time is 15 to 60 seconds.

9. The method according to claim 1, wherein the spraying time is 0.5 to 5 seconds.

10. The method according to claim 1, wherein the spraying time is 0.5 to 3 seconds.

* * * * *